(12) United States Patent
Su et al.

(10) Patent No.: US 6,492,540 B1
(45) Date of Patent: Dec. 10, 2002

(54) SOLVENTLESS NONTOXIC HIGH REFRACTION INDEX AND LOW BIREFRINGENCE ORGANIC/INORGANIC HYBRID MATERIALS

(75) Inventors: Wei-Fang Su, Taipei (TW); Hsiao-Kuan Yuan, Banchiau (TW)

(73) Assignee: Pole-Chic Corporation, Taipei (TW)

( * ) Notice: Subject to any disclaimer, the term of this patent is extended or adjusted under 35 U.S.C. 154(b) by 0 days.

(21) Appl. No.: 09/571,597

(22) Filed: May 15, 2000

(51) Int. Cl.[7] .............................. C07F 7/28; C07F 9/94; C07F 19/00

(52) U.S. Cl. .............................. 556/30; 556/55; 556/77

(58) Field of Search .............................. 556/77, 55, 30

(56) References Cited

U.S. PATENT DOCUMENTS

| | | | | |
|---|---|---|---|---|
| 2,502,411 A | * | 4/1950 | Neher et al. | 524/35 |
| 5,998,646 A | * | 12/1999 | Riondel et al. | 556/55 |
| 6,060,040 A | * | 5/2000 | Tournier et al. | 424/9.364 |

* cited by examiner

Primary Examiner—Porfirio Nazario-Gonzalez
(74) Attorney, Agent, or Firm—Troxell Law Office PLLC

(57) ABSTRACT

Enclosed are high refractive index and low birefringence organic/inorganic hybrid materials useful for optical applications. They are prepared from solventless metal aliphatic acryl alkoxides. The metal acryl alkoxides are synthesized from exchanging acryl alcohol with metal alkoxides, and are hydrolyzed into metal oxide nanoparticles and are well dispersed in the acrylate matrix. Then they are polymerized into organic/inorganic hybrid materials containing metal oxide in polyacrylate.

8 Claims, 3 Drawing Sheets

(1.8X10⁵)

(1.8X10⁵)

SOLVENTLESS NONTOXIC HIGH REFRACTION INDEX AND LOW BIREFRINGENCE ORGANIC/INORGANIC HYBRID MATERIALS

BACKGROUND OF THE INVENTION

1. Field of the Invention

The present invention relates to high refractive index and low birefringence organic/inorganic hybrid materials useful for optical applications.

2. Description of the Related Art

Many optical applications require high refractive index materials including filters, transmitters, reflectors, lenses, optical waveguides, sensors, devices, adhesives for optical components and device assembly, index matched materials for solid state laser, optical components.

The organic/inorganic hybrid materials have been used to prepare high refractive index materials. For examples, Wilkes et al. (U.S. Pat. No. 5,109,080) have been reported that a refractive index ranged from 1.60–1.76 can be obtained from a solvent based polyarylether(sulfone) containing $SiO_2$—$TiO_2$—$ZrO_2$. It is known that the aromatic moiety of polymer exhibits undesired birefringence properties for optical applications (Chem. & Eng. News p14–15, Dec. 20, 1999). The system also contained tetrahydrofuran and alcohol solvents. The tetrahydrofuran was used to dissolve polyarylether(sulfone) and the alcohol was used to obtain the metal oxide precursor solution. The solvents were also used (1) to carry out the reaction between organic component and inorganic component, and (2) to adjust the viscosity of the system for the ease of processing. However, the solvents create pollution problems during the processing. Zimmerman et al. (L. Zimmermann, M. Weibel, W. Caseri and U. W. Suter, J. Mater. Res., 8(7), 1993, p. 1742–48) prepared a gelatin-PbS system that has a refractive index range from 1.5 to 2.5. Kyprianidou-Leodidou et al (T. Kyprianidou-Leodidou, H-J. Althaus, Y. Wyser, D. Vetter, M. Bucher, W. Caseri and U. W. Suter, J. Mater. Res. 12(8), 1997, p. 2198–2206) synthesized high refractive index material from polyethyleneoxide-FeS (refractive index 2.5–2.8) and polyethyleneoxide-PbS (refractive index 3.9). However, gelatin and polyethyleneoxide are hydrophilic and absorb moisture easily, lack mechanical strength and dimensional stability. PbS is undesirable in the application due to its highly toxic nature of lead compound. Therefore, there is a need for an environmental friendly high refractive index, low birefringence and nontoxic organic/inorganic hybrid materials.

SUMMARY OF THE INVENTION

It is an object of the present application to provide high refractive index and low birefringence organic/inorganic hybrid materials are prepared by solventless metal aliphatic acryl alkoxides. The metal aliphatic acryl alkoxides are synthesized first. Then, the metal aliphatic acryl alkoxides are underwent hydrolysis to form nanoparticle metal oxides dispersed acrylates. They can be free radical polymerized (via thermal or photo) into high refractive index, low birefringence, high mechanical strength and low moisture absorption metal oxide dispersed aliphatic polyacrylates.

It is a further object of the present invention to provide organic/inorganic hybrid materials that are solventless, nontoxic, high refractive index, low birefringence, high mechanical strength and low moisture absorption.

It is an additional object of the present invention to provide a method of making organic/inorganic materials of present invention.

A more complete understanding of these and other features and advantages of the present invention will become apparent from a careful consideration of the following detailed description of certain embodiments and the illustrations as shown in the following drawings.

DETAILED DESCRIPTION OF THE PREFERRED EMBODIMENTS

Figure 1:
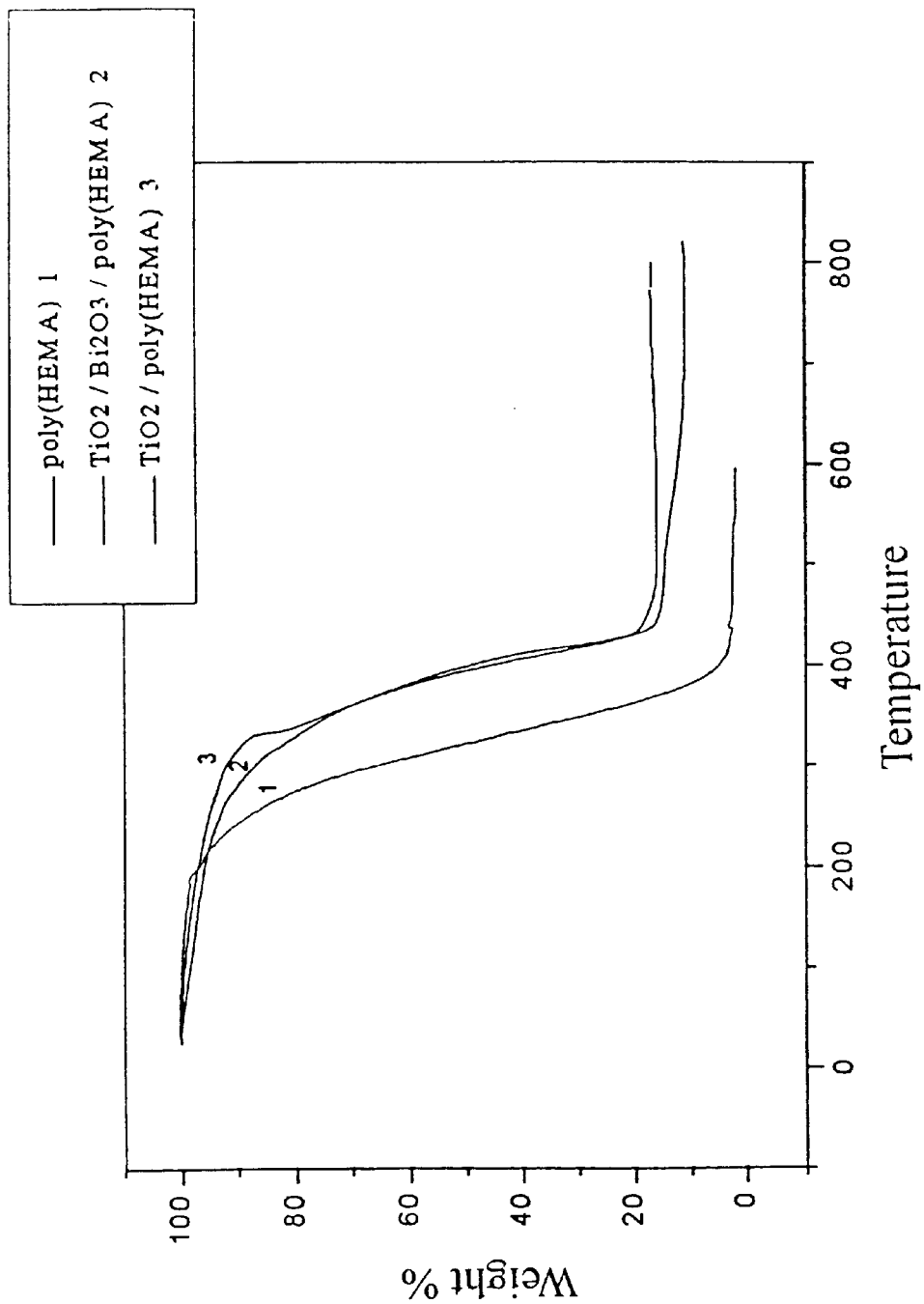
FIG. 1 is a thermogravimetric analysis of organic/inorganic hybrid materials.

Solventless high refractive index and low birefringence organic/inorganic hybrid materials are prepared by three steps. The first step is to synthesize solventless metal aliphatic acryl alkoxides. The second step is to hydrolyze the metal aliphatic acryl alkoxides and form nanoparticle metal oxides dispersed acrylates. The third step is to free radical polymerize (via thermal or photo) the acrylates by free radical polymerization into high refractive index, low birefringence, high mechanical strength and low moisture absorption metal oxide dispersed aliphatic polyacrylates.

In the first step, the solventless metal aliphatic acryl alkoxides are synthesized. They have the general formula of $M[-OR_1-O-CO-C(R_2)=CR_3R_4]_n$. Where the M is a metal element or a mixture of metal elements. The metal can be selected from the metals in the periodic table except toxic metal such as lead. The metals with the atomic number greater than the silicon element is preferred. The n value is dependent on the valence of metal. Where R1 is a straight chain alkyl group or branched alkyl group. The straight chain is preferred with the formula of (—CH2—)n. Where n is equal to 1 to 12 and n is equal to 1 to 4 is preferred. Where R2, R3, R4 can be a hydrogen atom or straight chain alkyl group (—CH2—)n or branched alkyl group. The straight chain alkyl group is preferred, n is equal to 1 to 12 and n is equal to 1 to 4 is preferred. The metal aliphatic acryl alkoxides are synthesized either by reacting metal with acrylate alcohol or by reacting metal alkoxide with acrylate alcohol through an alcohol exchange. The alcohol exchange is preferred, so a wide range of metal type can be selected. The alcohol exchange reaction is shown in the equation (1):

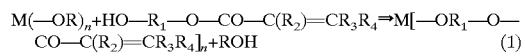  (1)

Where R is a straight chain alkyl group or branched alkyl group. The straight chain is preferred with the formula of $(-CH_2-)_n$. Where n is equal to 1 to 12 and n is equal to 1 to 4 is preferred. The reaction can be carried out in a moderate temperature such as 50 to 100° C. with or without catalysts. The catalysts are acids or bases. They can be inorganic catalysts or organic catalysts. The inorganic acid catalysts include HF, HBr, HCl, $HNO_3$ and $H_2SO_4$, and other mineral acids. The organic acid catalysts include aliphatic or aromatic carboxylic acids, etc. The inorganic bases include $NH_4OH$, NaOH, KOH, etc. The organic bases include aliphatic or aromatic amines, etc. The preferred reaction conditions are 60° C. reflux without catalyst under the absolute dry and inert gas conditions (~0% relative humidity) such as dry argon or dry nitrogen. The nitrogen is preferred due to its low cost. The byproduct ROH was removed by a vacuum distillation.

In the second step, the metal acryl alkoxides are underwent acid or base catalyzed hydrolysis to form nanoparticle metal oxides dispersed acrylate monomers. The hydrolysis reaction is shown in the equation (2).

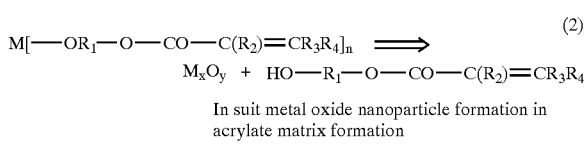

(2)

$$M[-OR_1-O-CO-C(R_2)=CR_3R_4]_n \Longrightarrow$$
$$M_xO_y + HO-R_1-O-CO-C(R_2)=CR_3R_4$$

In suit metal oxide nanoparticle formation in acrylate matrix formation

The equation (2) is a hydrolysis reaction, which is carried out in the acid, or base catalyzed condition to form metal oxide nanoparticles in suit in the acrylate monomer at room temperature. The catalysts can be inorganic or organic based catalysts as mentioned in the reaction (1). The formation of metal oxide particles is through the chemical reaction, so they can be nano size and dispersed evenly in the acrylate matrix. The nano size of particle is important, so the material can be transparent in visible light with high light transmission.

In the third step, the acrylate monomers are polymerized into polyacrylates via thermal or photo initiated free radical polymerization according to equation (3):

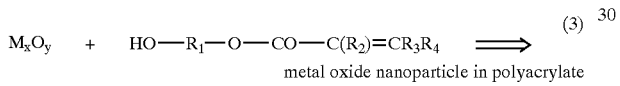

(3)

$$M_xO_y + HO-R_1-O-CO-C(R_2)=CR_3R_4 \Longrightarrow$$
metal oxide nanoparticle in polyacrylate The polymerization can be carried out either by thermal induced or photo induced radical polymerization. For thermal induced polymerization, a thermal initiator or a mixture of thermal initiators is required. Peroxides, disulfides, diazo compounds are well known to those skilled in the art of thermal initiators. The diazo compounds of 2,2'-azobisisobutyronitrile (AIBN) is preferred. The weight percentage of 0.1–1.0 of thermal initiator can be used. The reaction is carried out in a moderate temperature ranged from 50 to 100° C. for several hours. For photo induced polymerization, a photo initiator or a mixture of photo initiators is required. Benzoin ether derivatives, benzophenone derivatives, acetophenone derivatives are well known to those skilled in the art of photo initiators. 2,2-dimethoxy-2-phenyl acetyl phenone, sold as Irg 651 by Ciba-Geigy is preferred. The weight percentage of 0.5–5 of photo initiator can be used. A UV light source is used to carry out the reaction from several seconds to several minutes. For a thin film sample (<1 mm thickness), the photo initiation is preferred. The thin film is prepared by a spin coating method. For a bulk sample (>1 mm thickness), the thermal initiation is preferred for a through cure of thick area. The bulk material is prepared by casting in a mold method. The refractive index of the material is measured by an Ellipsometer (Gaer Tner Model 116C) in the visible range (400–1000 nm). The optical transmission of the materials is measured by a UV-Vis spectrophotometer (Jasco H-7100))

The following examples further illustrate this invention:

EXAMPLE 1

Preparation of Titanium Methacryl Ethoxide

In a dry nitrogen glove box, 100 ml of dry tetrahydrofuran, 10.33 grams of titanium n-propoxide were placed in a 250 ml flask and mixed them well at room temperature. The 18.73 grams of hydroxy ethyl methacrylate were added into the mixture and reacted at room temperature. As soon as the solution became golden yellow, a vacuum distillation was used to remove propanol by product. The distillation was continued for 12 hours to remove tetrahydrofuran and propanol completely. A solventless titanium methacryl ethoxide was obtained. The structure of the product was identified by NMR and IR.

EXAMPLE 2

Preparation of Titanium Bismuth Methacryl Ethoxide

In a dry nitrogen glove box, 1.5 grams of titanium methacrylate ethoxide prepared from example 1, 8.16 grams of hydroxy ethyl methacrylate and 2–3 drops of water were mixed for 10 min in a flask. The 13.5 grams of $1.7 \times 10^{-4}$ mole of bismuth methoxy ethoxide in tetrahydrofuran was added into the mixture and reflux at 60° C. for one hour. A vacuum distillation was used to remove tetrahydrofuran and methoxy ethanol by product at room temperature for 8 hours. A solventless titanium bismuth methacryl ethoxide was obtained. The structure of the product was identified by NMR and IR.

EXAMPLE 3

Preparation of Film Sample

An about 20 grams of 10% (vol.) aqueous hydroxy ethyl methacrylate was added into a mixture of 100 grams (96 gram of metal methacryl ethoxide and 4 gram of 2,2-dimethoxy-2-phenyl acetophenone (photoinitiator)) to hydrolyze the mixture. The exact amount of water used in the hydrolysis was dependent on the gel rate of the mixture. The mixture was hydrolyzed for 2 minutes, and then the hydrolyzed mixture was spin coated on a Si wafer substrate. The sample was irradiated with an UV light (UVP Co. Model UVGL-25) at 254 nm for 3 min. and 365 nm for 3 min to cure the film.

EXAMPLE 4

Preparation of Monolith Sample

The photoinitiator of above mixture was replaced by a 0.5 wt % of 2,2'-azobis (isobutyronitrile) thermal initiator. The mixture was poured into a mold with a dimension of 1 cm in diameter and 3 mm in thickness. The hydrolysis time was increased from the above film sample time 2 minutes to 30 minutes, then the hydrolyzed sample was cured at 50° C./6 hrs, 60° C./24 hrs and 90° C./48 hrs.

EXAMPLE 5

Characterization of Organic/Inorganic Hybrid Materials a. Refractive Index Measurement The refractive index of the cured film was measured by an Ellipsometer (Gaer Tner Co.). The results are shown in Table 1

TABLE 1

Refractive Index of Organic/Inorganic Hybrid Materials.

| Material | Refractive Index |
|---|---|
| Polyhydroxyethylmethacrylate-TiO$_2$ | 1.61 |
| Polyhydroxyethylmethacrylate-TiO$_2$/Bi$_2$O$_3$ | 1.69 |
| Polyhydroxyethylmethacrylate | 1.51 |

The refractive index of the neat polymer: polyhydroxyethylmethacrylate has been increased from 1.51 to 1.61 for TiO$_2$ dispersed polymer and to 1.69 for TiO$_2$/Bi$_2$O$_3$ dispersed polymer.

b. Thermogravimetric Analysis

The sample was analyzed at 5° C./min from room temperature to 800° C. in nitrogen using DuPont 9900 TGA 954 instrument. The results are shown in FIG. 1. The hybrid materials have shown an improved thermal stability; for a 10% weight loss temperature, the hybrid materials have a higher decomposition temperature (325° C.) than that of (250° C.) neat acrylate polymer.

c. The Optical Transmission Spectrum Analysis

Figure 2:
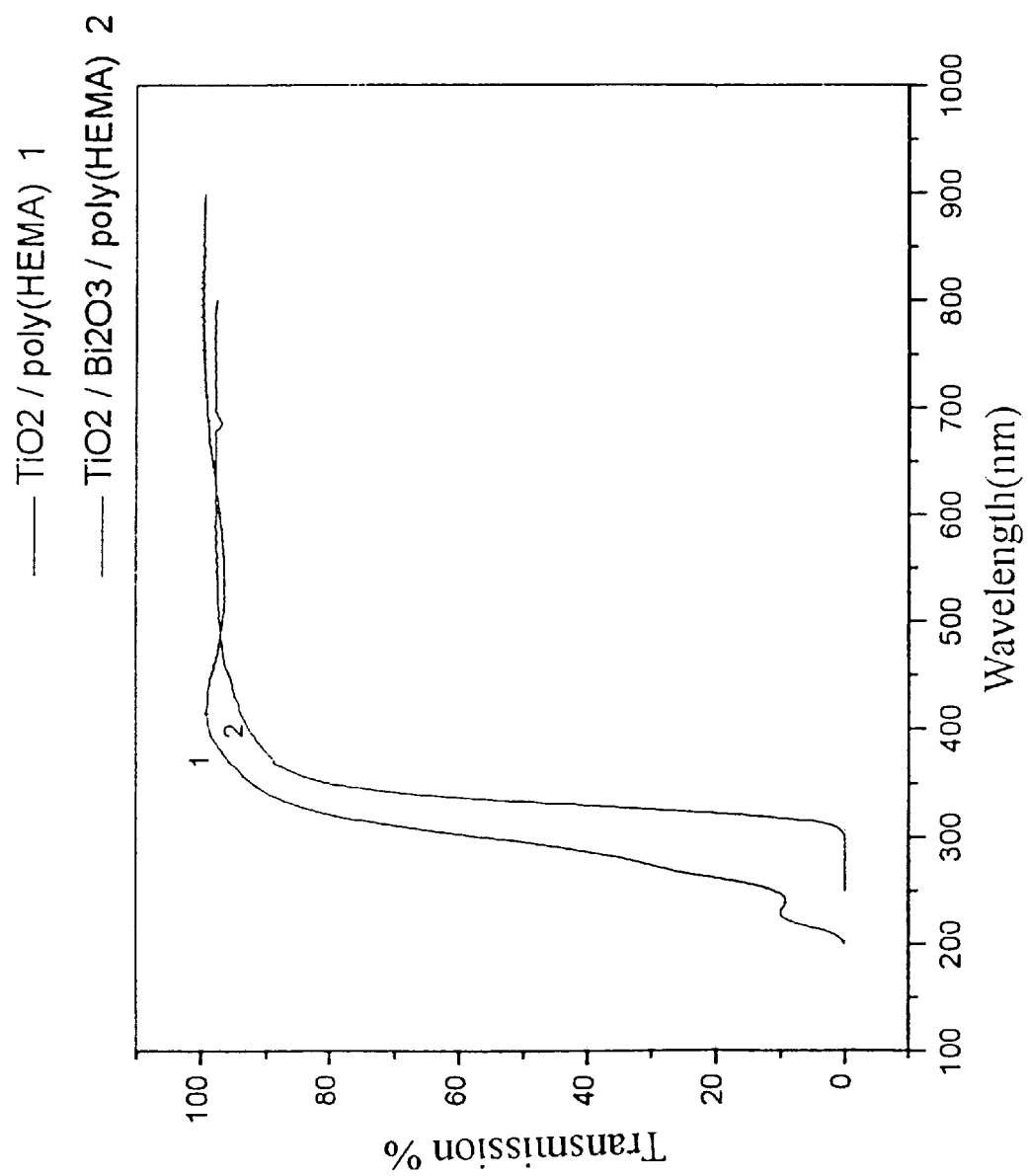
FIG. 2 is a UV-VIS spectra of organic/inorganic hybrid materials.

The UV-VIS transmission spectra were measured by Jasco H-7100. The results are shown in FIG. 2. Both samples exhibited more than 95% transmission in the visible region.

d. Transmission Electron Microscope (TEM) Analysis

Figure 3:
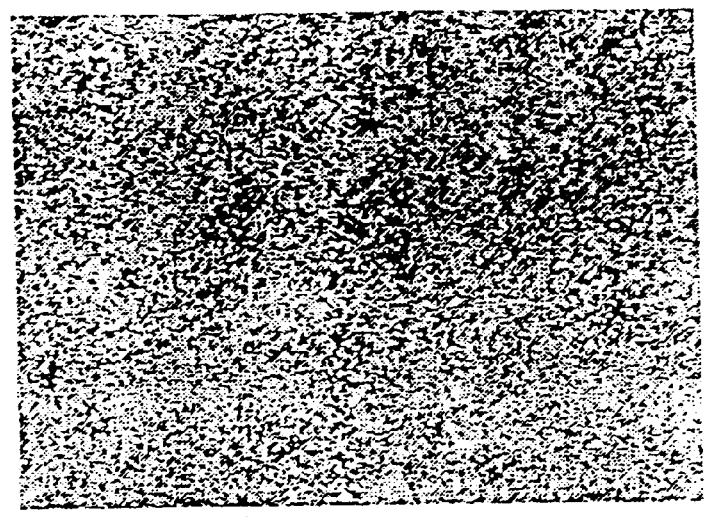
FIG. 3 is a TEM photo of $TiO_2$/polyacrylate.
Figure 4:
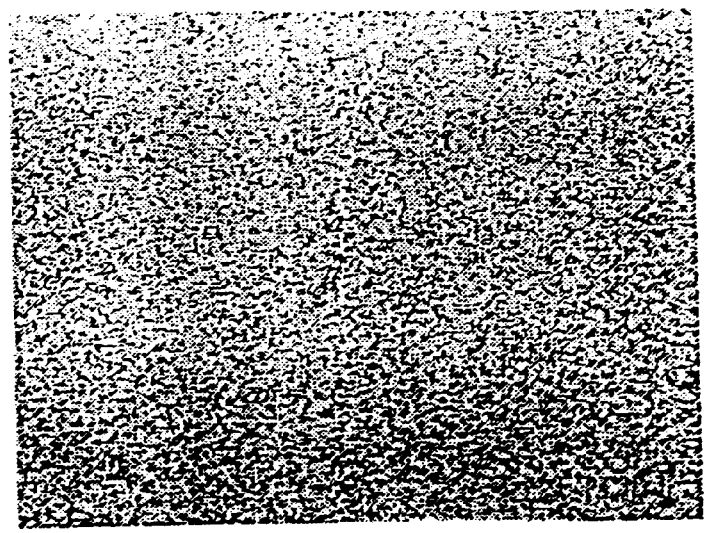
FIG. 4 is a TEM photo of $TiO_2$/$Bi_2O_3$/polyacrylate.

Hitachi H-7100 instrument was used to analyze the samples. The results are shown in FIG. 3 and FIG. 4. Both of the materials are shown the metal oxides are well dispersed in the polyacrylate matrix. The size of the metal oxides is in the range of 10–20 nm, which is smaller than the size of visible light, so the samples are transparent.

Whereas particular embodiments of the invention have been described above for purposes of illustration, it will be appreciated by those skilled in the art that numerous variations of the details may be made without departing from the invention as described in the appended claims.

What we claim is:

1. A compound metal aliphatic acryl alkoxide having the general formula of $M[-OR_1-O-CO-C(R_2)=CR_3R_4]_n$ wherein said compound is prepared for exchanging acryl alcohol $HO-R_1-O-CO-CR_2=CR_3R_4$ with metal alkoxide $M[-O-(R)-(O)a-(R)_b-CH_3]_n$, and wherein M is a metal element or a mixture of metal elements, $R_1$ is an alkyl group, $R_2R_3R_4$ is a hydrogen atom or an alkyl group, a is equal to 0 or 1, b is equal to 0 to 12, and n is equal to 1 to 12.

2. A compound as claimed in claim 1 wherein $R_1$ is a straight chain alkyl group or branched alkyl group; the straight chain is preferred with the formula of $(-CH_2-)_n$, where n is preferably equal to 1 to 4 and $R_2$, $R_3$, $R_4$ can be a hydrogen atom or straight chain alkyl group $(-CH_2-)_n$ or branched alkyl group.

3. A compound as claimed in claim 1, wherein the acryl alcohol $HO-R_1-O-CO-C(R_2)=CR_3R_4$ is $HO-CH_2CH_2-O-CO-C(CH_3)=CH_2$.

4. A compound as claimed in claim 1, wherein in metal alkoxide $M[-O-(R)-(O)a-(R)_b-CH_3]_n$, the metal M is selected from the metals in the periodic table except toxic metal such as lead; the metals with the atomic number greater than the silicon element are preferred such as titanium or bismuth; while R is a straight chain alkyl groups or branched alkyl groups; the straight chain is preferred with the formula of $-(CH_2-)_x$, where x is preferably equal to 1 to 4, and b is preferably equal to 0 to 4.

5. A compound as claimed in claim 1, wherein the metal alkoxide $M[-O-(R)-(O)a-(R)_b-CH_3]_n$ is $Ti[-O-(CH_2)_3CH_3]_4$, or $Bi[-O-(CH_2)_2-OCH_3]_3$.

6. A compound metal aliphatic acryl alkoxide obtained from the alcohol exchanging reaction as claimed in claim 1, wherein said compound is $Ti[-OCH_2CH_2-O-CO-C(CH_3)=CH_2]_4$.

7. A compound metal aliphatic acryl alkoxide obtained from the alcohol exchanging reaction as claimed in claim wherein said compound is $Bi[-OCH_2CH_2-O-CO-C(CH_3)=CH_2]_3$.

8. A compound metal aliphatic acryl alkoxide obtained from the alcohol exchanging reaction as claimed in claim 1, wherein said compound is a mixture of $Ti[-OCH_2CH_2-O-CO-C(CH_3)=CH_2]_4$ and $Bi[-O-CH_2CH_2-O-CO-C(CH_3)=CH_2]_3$ with the composition of $\{Ti(-O-CH_2CH_2-O-CO-C(CH_3)=CH_2)_4\}_{1.5}\{Bi[-OCH_2CH_2-O-CO-C(CH_3)=CH_2]_3\}_1$.

* * * * *